US012691153B2

(12) United States Patent (10) Patent No.: US 12,691,153 B2
Lin et al. (45) Date of Patent: Jul. 28, 2026

(54) METHOD FOR IMPROVING BONE HEALTH BY USING MANGOSTEEN SHELL EXTRACT

(71) Applicant: TCI CO., LTD., Taipei (TW)

(72) Inventors: Yung-Hsiang Lin, Taipei (TW);
Chung-An Tien, Taipei (TW)

(73) Assignee: TCI CO., LTD., Taipei (TW)

( * ) Notice: Subject to any disclaimer, the term of this patent is extended or adjusted under 35 U.S.C. 154(b) by 303 days.

(21) Appl. No.: 18/670,739

(22) Filed: May 22, 2024

(65) Prior Publication Data

US 2024/0390441 A1 Nov. 28, 2024

Related U.S. Application Data

(60) Provisional application No. 63/503,503, filed on May 22, 2023.

(51) Int. Cl.
| | |
|---|---|
| *A61K 36/00* | (2006.01) |
| *A61K 8/9789* | (2017.01) |
| *A61K 9/00* | (2006.01) |
| *A61K 36/22* | (2006.01) |
| *A61K 36/38* | (2006.01) |
| *A61P 17/14* | (2006.01) |
| *A61P 19/00* | (2006.01) |
| *A61P 29/00* | (2006.01) |
| *A61P 39/06* | (2006.01) |
| *A61Q 7/00* | (2006.01) |

(52) U.S. Cl.
CPC ........... *A61K 36/38* (2013.01); *A61K 8/9789* (2017.08); *A61K 9/0095* (2013.01); *A61K 36/22* (2013.01); *A61P 17/14* (2018.01); *A61P 19/00* (2018.01); *A61P 29/00* (2018.01); *A61P 39/06* (2018.01); *A61Q 7/00* (2013.01); *A61K*

*2236/39* (2013.01); *A61K 2236/51* (2013.01); *A61K 2800/92* (2013.01)

(58) Field of Classification Search
CPC ..................................................... A61K 36/38
See application file for complete search history.

(56) References Cited

FOREIGN PATENT DOCUMENTS

CN 105130944 A * 12/2015 ........... C07D 311/62

OTHER PUBLICATIONS

Examination report dated Feb. 5, 2025, listed in correspondent Taiwan patent application No. 113118982 (publication No. 202446408).
Utari Kresnoadi et al., Effects of mangosteen peel extract combined with demineralized freeze-dried bovine bone xenograft on osteocalcin, collagen 1, and osteoblast as alveolar bone regeneration in socket preservation. vol. 18, Issue 2. The Journal of Indian Prosthodontic Society, Apr-Jun. 2018. 117-121 Fourth paragraph of the left col. of p. 118, paragraph of Research procedure, p. 119, conclusion, Figs. 1-3.
Ruixue Liu et al., Enzyme-Assisted Ultrasonic Extraction of Total Flavonoids from Acanthopanax senticosus and Their Enrichment and Antioxidant Properties. vol. 9, Issue 10, Processes, Sep. 23, 2021. pp. 1-14 Abstract, paragraph 2 of p. 2, methods, paragraph of 3.1.5-3.1.6, first paragraph of discussion.

* cited by examiner

*Primary Examiner* — Qiuwen Mi
(74) *Attorney, Agent, or Firm* — Chieh-Mei Wang

(57) ABSTRACT

A method for improving bone health is provided, including administering to a subject in need thereof a composition including a mangosteen shell extract. The mangosteen shell extract is prepared by performing a two-stage extraction on a fruit shell of mangosteen (*Garcinia mangostana*) using an enzyme solution at different extraction temperatures sequentially.

13 Claims, 6 Drawing Sheets
(3 of 6 Drawing Sheet(s) Filed in Color)

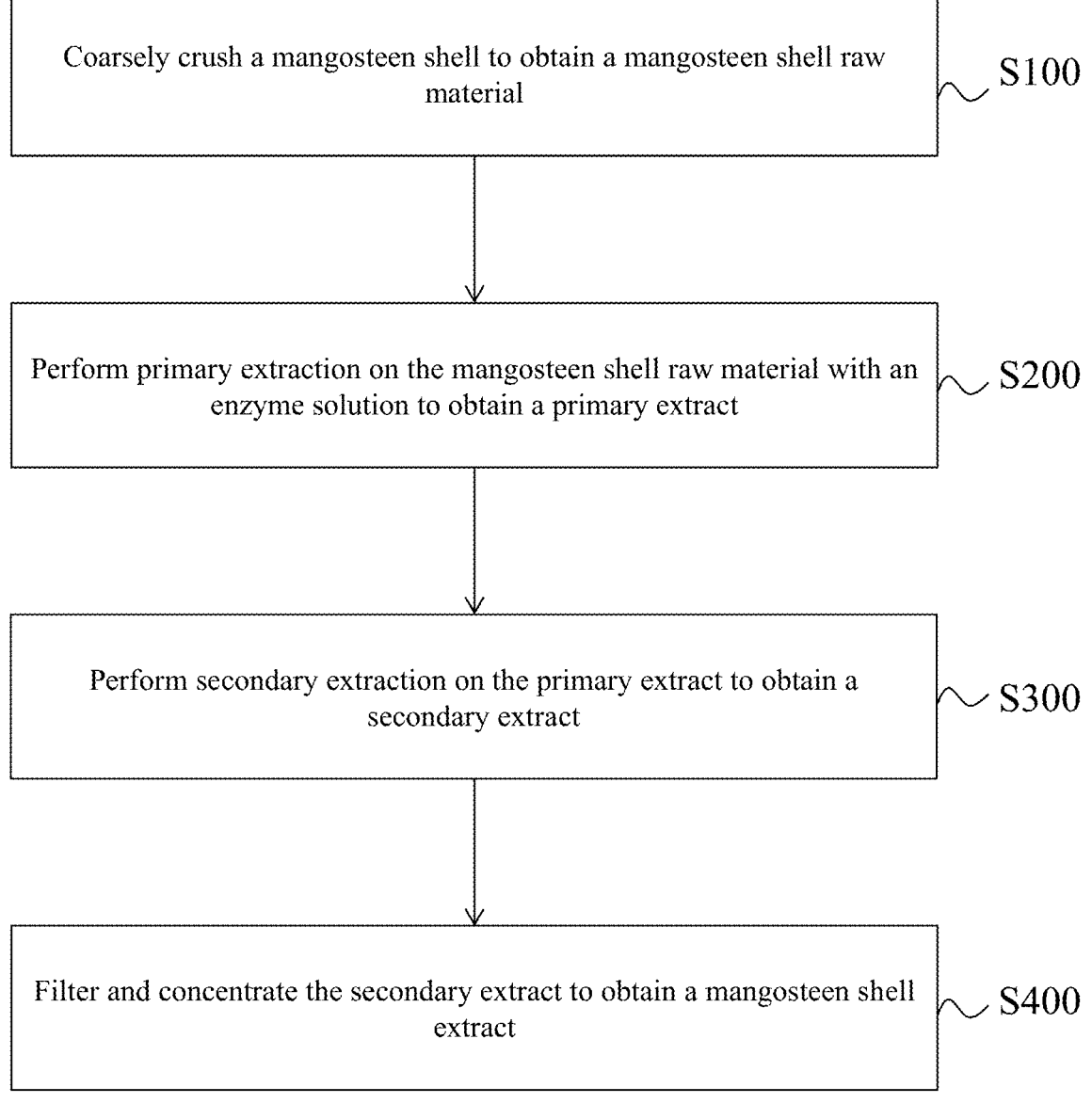

Coarsely crush a mangosteen shell to obtain a mangosteen shell raw material ⟩ S100

Perform primary extraction on the mangosteen shell raw material with an enzyme solution to obtain a primary extract ⟩ S200

Perform secondary extraction on the primary extract to obtain a secondary extract ⟩ S300

Filter and concentrate the secondary extract to obtain a mangosteen shell extract ⟩ S400

FIG. 1

Control group                    Experimental group

METHOD FOR IMPROVING BONE HEALTH BY USING MANGOSTEEN SHELL EXTRACT

CROSS-REFERENCE TO RELATED APPLICATION

This application claims the benefit of U.S. provisional application Ser. No. 63/503,503, filed on May 22, 2023. The entirety of the above-mentioned patent application is hereby incorporated by reference herein and made a part of the specification.

BACKGROUND

Technical Field

The present invention relates to use of a mangosteen shell extract, and in particular, to use of a mangosteen shell extract prepared from a mangosteen shell for improving bone health.

Related Art

Approximately 200 million people worldwide are affected by osteoporosis symptoms in modern society. Statistically, approximately 8.9 million cases of fragility fractures occur every year, where about one third of women and one fifth of men over the age of 50 suffer from fragility fractures through their whole life.

In addition, more than half a billion people worldwide suffer from degenerative arthritis every year. With the increase in the elderly population, people suffering from arthritis increase by 48% in nearly 30 years until 2019. Symptoms of arthritis and soft-tissue inflammation include wear and tear of cartilage between bones, structural deformation, or reduced secretion of synovial fluid between joints, causing pain, swelling, warmth, and stiffness at the joints.

Orthopedic surgeons point out that symptoms of osteoporosis are substantially irreversible. Once bone loss occurs, subsequent treatment and prevention can only slow down the bone loss at best. However, treatment for arthritis is mainly to relieve the burden and pain of joints, instead of restoring to a previous bone state and joint mobility.

Therefore, in recent years, bone health has been gradually emphasized by the public, and bone health includes not only bone strengthening and joint mobility improvement, but also assistance to muscles for the movement of bones and joints. To resolve the foregoing problems, there is an urgent need for a person skilled in the art to develop functional food that can resolve the foregoing problems, for the benefit of the general public who have such needs.

SUMMARY

In some embodiments, a method for improving bone health is provided, including administering to a subject in need thereof a composition including a mangosteen shell extract, wherein the mangosteen shell extract is prepared by performing two-stage extraction on a fruit shell of mangosteen (*Garcinia mangostana*) using an enzyme solution at different extraction temperatures sequentially.

In some embodiments, use of a mangosteen shell extract for preparing a composition for improving bone health is provided. The mangosteen shell extract is prepared by performing two-stage extraction on a fruit shell of mangosteen (*Garcinia mangostana*) using an enzyme solution at different extraction temperatures sequentially.

In some embodiments, the extraction temperatures for the two-stage extraction are 45° C. to 65° C. and 75° C. to 95° C. respectively.

In some embodiments, extraction time at each stage of the two-stage extraction is 60 minutes to 90 minutes.

In some embodiments, performing the two-stage extraction includes the following steps: performing a primary extraction on the fruit shell of mangosteen with the enzyme solution at 45° C. to 65° C. for 60 minutes to obtain a primary extract; performing a secondary extraction on the primary extract at 75° C. to 95° C. for 60 minutes to 90 minutes to obtain a secondary extract; and filtering and concentrating the secondary extract, to obtain the mangosteen shell extract.

In some embodiments, the extraction temperature for the primary extraction is 55±5° C., and the extraction temperature for the secondary extraction is 85±5° C.

In some embodiments, the enzyme solution is an aqueous solution containing 0.1-1 wt % of diastase.

In some embodiments, the diastase is glucoamylase, α-amylase, β-amylase, isoamylase, or any combination thereof.

In some embodiments, the mangosteen shell extract has a total flavonoid content of at least 19000±5000 ppm.

In some embodiments, the bone health is bone strengthening, joint wear and tear prevention, and/or bone loss prevention.

In some embodiments, the mangosteen shell extract has at least one of the following functions: inhibiting osteoclast differentiation, increasing bone density, promoting intestinal calcium absorption, and promoting osteocalcin secretion, so as to strengthen the bones.

In some embodiments, the mangosteen shell extract has at least one of the following functions: promoting polyglucosamine expression and reducing inflammation, so as to prevent joint wear and tear.

In some embodiments, the mangosteen shell extract has at least one of the following functions: inhibiting osteoclast differentiation and promoting osteocalcin secretion, so as to prevent bone loss.

In some embodiments, the mangosteen shell extract has a function of relieving inflammation in the body of the subject in need thereof.

Based on the above, the mangosteen shell extract in any one of the embodiments of the present disclosure has an effect of improving bone health. In addition, the mangosteen shell extract is prepared by a two-stage extraction at different extraction temperatures, to fully release the active ingredients from the mangosteen shell and increase the contents of the active ingredients in the mangosteen shell extract. In some embodiments, the mangosteen shell extract has the effects of strengthening bones, preventing joint wear and tear, relieving bone loss, improving calcium absorption, relieving inflammation in the body, and preventing inflammation caused by joint wear and tear.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a flowchart of preparing a mangosteen shell extract according to any one of the embodiments;

DETAILED DESCRIPTION

Figure 2:
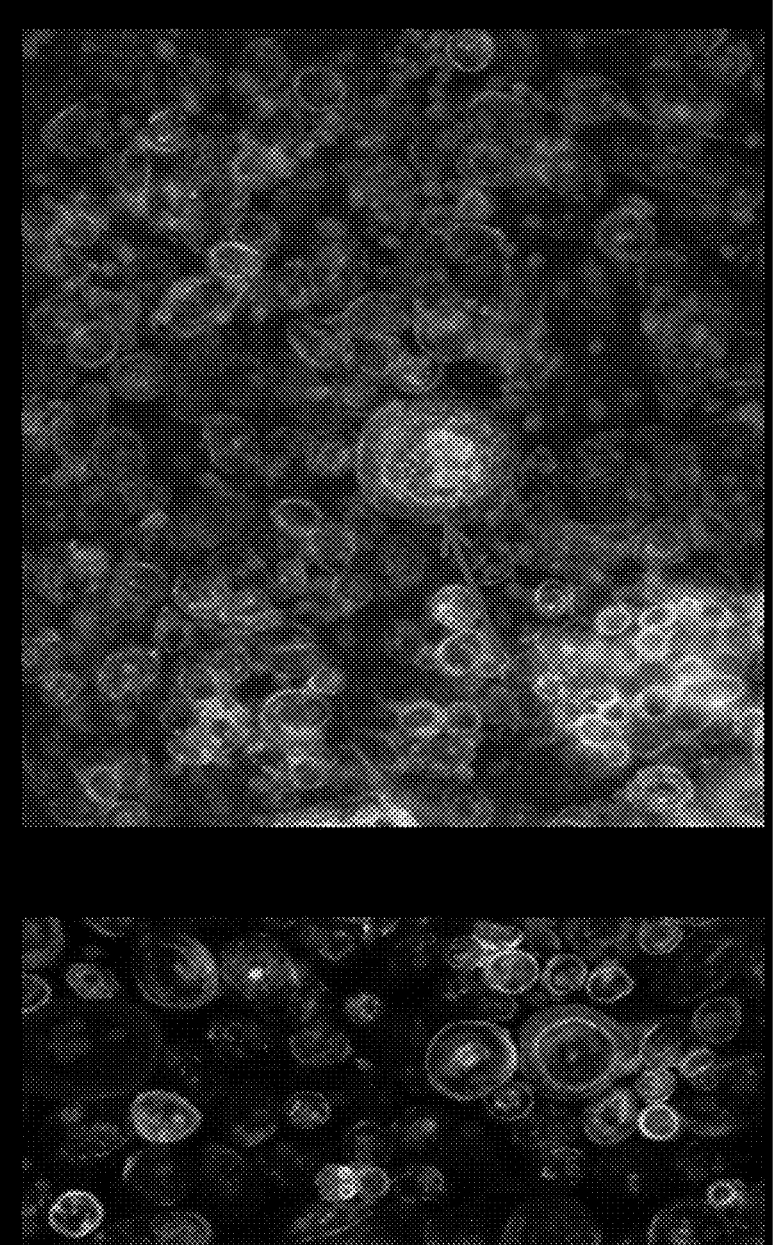
FIG. 2 shows photographs of an experimental group and a control group in an osteoclast differentiation inhibition experiment.

The following describes some specific implementations of the present disclosure. Without departing from the spirit of the present invention, the present invention may be implemented in many different forms of embodiments, and the protection scope should not be limited to conditions specified in this specification.

Mangosteen (*Garcinia mangostana*), also known as the purple mangosteen, is a species under the genus *Garcinia* in the family Clusiaceae. The mangosteen tree is a tropical evergreen tree native to the Sunda and Moluccas Islands in the Malay Archipelago. A ripe mangosteen fruit is of a spherical shape of 4-8 cm in diameter, with smooth epidermis, fleshy sepals, and a stigma remaining in the inner layer of the exocarp. The exocarp of the mangosteen fruit is black in color and bitter in taste, which is inedible, while the flesh is white and garlic-like, and is sweet and mild in odor and taste.

A mangosteen shell extract is obtained by mixing a fruit shell of mangosteen (*Garcinia mangostana*) (hereinafter referred to as mangosteen shell) with an extraction solvent at a specific ratio and performing two-stage extraction respectively at different extraction temperatures for a period of time. In some embodiments, the used mangosteen shell may be a fruit shell of ripe mangosteen (*Garcinia mangostana*).

In some embodiments, referring to FIG. 1, first, an obtained mangosteen shell is coarsely crushed into mangosteen shell fragments or granules (hereinafter referred to as mangosteen shell raw material) (step S100). In some embodiments, the mangosteen shell raw material is mangosteen shell fragments of about 12 mm in size obtained by cutting and coarsely crushing the mangosteen shell. For example, the cut-up mangosteen shell is filtered through a sieve with a pore size of 12 mm, to obtain the mangosteen shell raw material for extraction. Herein, it can be ensured through screening by using a sieve with a specific pore size that the size of the mangosteen shell fragments meets a requirement, to further increase a contact area with a solvent in a subsequent extraction step.

After step S100, the mangosteen shell raw material and an enzyme solution are mixed to perform a primary extraction on the mangosteen shell raw material with the enzyme solution, to obtain a primary extract (step S200). The enzyme solution is an aqueous solution containing 0.1-1 wt % (for example, 0.5 wt %) of diastase. For example, the enzyme solution is obtained by dissolving diastase in RO water. The diastase may be, but is not limited to, glucoamylase, α-amylase, β-amylase, isoamylase, or any combination thereof. In some embodiments, a weight ratio of the mangosteen shell raw material to the enzyme solution is (0.2-5):(1-10) (for example, 1:4). In some embodiments, an extraction temperature for the primary extraction is 45° C. to 65° C. (for example, 55±5° C.), and extraction time for the primary extraction is 60 minutes to 90 minutes. For example, after the temperature of the enzyme solution is increased to the extraction temperature for the primary extraction, the mangosteen shell raw material is added to perform the primary extraction, to obtain the primary extract.

After step S200, a secondary extraction is performed on the primary extract to obtain a secondary extract (step S300). In some embodiments, an extraction temperature for the secondary extraction is 75° C. to 95° C. (for example, 85±5° C.), and extraction time for the secondary extraction is 60 minutes to 90 minutes. For example, after the temperature of the primary extract is increased to the extraction temperature for the secondary extraction, the secondary extraction is performed, to obtain the secondary extract. In some embodiments, a degree Brix (° Bx) of the secondary extract obtained through the secondary extraction is greater than 1.3° Bx (detected at 20° C.). In some examples, after the temperature of the primary extract is increased to 85±5° C., extraction is performed for 60 minutes, and whether degree Brix of the current secondary extract meets the requirement (that is, whether the degree Brix is greater than 1.3) is detected at the 60th minute. If the degree Brix does not meet the requirement, the extraction may be continued for 30 minutes, and then the degree Brix is detected again.

Herein, an extraction solvent and a to-be-extracted substance in a specific ratio, a to-be-extracted substance of a specific size (for example, a crushed fruit shell), stage-specific extraction temperature and time, or any combination thereof can significantly increase extraction efficiency. Further, the specific extraction temperature can help release active ingredients more fully from the raw material, and the specific extraction time can avoid possible degradation of active ingredients in the extract caused by excessively long extraction time.

In some embodiments, after step S300, the secondary extract is filtered and concentrated to obtain a mangosteen shell extract (step S400). In some embodiments, the filtering step is filtering the secondary extract through a filter screen with a specific pore size, to filter out extracted mangosteen shell fragments. In some embodiments, the concentration is concentrating the filtered secondary extract under reduced pressure with vapor at a specific temperature and pressure, and whether a degree Brix of a concentrate meets the requirement is detected to determine whether the mangosteen shell extract is obtained. In some embodiments, a degree Brix of the mangosteen shell extract is 6.0±0.5° Bx (detected at 20° C.). In some examples, after the secondary extract is filtered through a 400-mesh filter screen, the filtered secondary extract is concentrated with 1±0.2 kg/cm² vapor at 55° C. to 65° C. (for example, 60±5° C.), until the degree Brix is 6.0±0.5° Bx (detected at 20° C.), to obtain the mangosteen shell extract.

In some embodiments, the mangosteen shell extract has a total flavonoid content of at least 19000±5000 ppm.

In some embodiments, the mangosteen shell extract has an effect of improving bone health. For example, the mangosteen shell extract can strengthen bones, prevent joint wear and tear, and/or relieve bone loss.

In some embodiments, in addition to strengthening bones, preventing joint wear and tear, and/or preventing bone loss, the mangosteen shell extract can further help improve joint mobility and assist muscles for the movement of bones and joints.

In some embodiments, the mangosteen shell extract has at least one of the following functions: inhibiting osteoclast differentiation, increasing bone density, promoting polyglucosamine expression, promoting intestinal calcium absorption, promoting osteocalcin secretion, and reducing inflammation.

It should be understood that a subject described below is an object to whom the mangosteen shell extract is administered invasively (for example, injection) or non-invasively (for example, consumption). In some embodiments, the subject is a human.

In some embodiments, the mangosteen shell extract can effectively inhibit osteoclast differentiation and reduce the quantity of mature osteoclasts in the subject, to strengthen bone quality and increase bone density. In some embodiments, the mangosteen shell extract can increase bone density to strengthen bones.

In some embodiments, the mangosteen shell extract can increase an absorption rate (for example, 10%) of calcium in the intestinal tract of the subject, to strengthen bones and bone quality. In addition, a probability that the human body absorbs calcium from the bones when calcium intake is insufficient can be avoided or reduced.

In some embodiments, the mangosteen shell extract can promote osteocalcin secretion, to increase the concentration of osteocalcin in the blood and help bone formation. Specifically, osteocalcin is mainly produced by osteoblasts, and the content of osteocalcin is positively correlated with bone formation. Usually, a higher concentration of osteocalcin indicates better bone synthesis. Therefore, the mangosteen shell extract promotes osteocalcin secretion of the subject, which can help bone formation of the subject.

For example, the mangosteen shell extract has at least one of the following functions: inhibiting osteoclast differentiation, increasing bone density, promoting intestinal calcium absorption, and promoting osteocalcin secretion, to achieve an effect of strengthening bones. For example, the mangosteen shell extract has at least one of the following functions: inhibiting osteoclast differentiation and promoting osteocalcin secretion, to achieve an effect of relieving bone loss.

In some embodiments, the mangosteen shell extract can promote polyglucosamine expression in the subject, to reduce cartilage wear and tear and keep joints from wearing and tearing.

In some embodiments, the mangosteen shell extract can relieve inflammation in the body. For example, administration of the mangosteen shell extract to the subject can reduce the concentration of high-sensitivity C-reactive protein (hs-CRP) in the body. The hs-CRP is a special protein produced by liver cells. When the body is injured, infected, or inflamed, the concentration of hs-CRP in the blood increases, which is one of the indicators of inflammation. For inflammation due to bone friction caused by articular cartilage wear and tear, administration of the mangosteen shell extract can relieve inflammation in the body and further reduce joint pain. In addition, studies have found that during bone metabolism and bone turnover, an inflammatory response has a significant impact on bone physiology and bone remodeling, inducing osteoporosis. Therefore, the mangosteen shell extract relieves inflammation in the body, thereby reducing a probability of inducing osteoporosis.

For example, the mangosteen shell extract has at least one of the following functions: promoting polyglucosamine expression and reducing inflammation, to achieve an effect of preventing joint wear and tear.

In some embodiments, the mangosteen shell extract may be prepared for enteral or oral administration by using techniques well known to a person skilled in the art.

In some embodiments, a dosage form for enteral or oral administration may be, but is not limited to, a tablet, a troche, a lozenge, a pill, a capsule, dispersible powder or granules, a solution, a suspension, an emulsion, syrup, an elixir, slurry, or the like.

In some embodiments, any composition described above may be an edible product. In other words, the edible product includes a specific content of mangosteen shell extract. In some embodiments, the edible product may be common food, health food, or a dietary supplement.

In some embodiments, the edible product may be prepared into a dosage form for oral administration by using techniques well known to a person skilled in the art. In some embodiments, the common food may be the edible product itself. In some embodiments, the common food may be, but is not limited to, beverages, fermented foods, bakery products, or flavorings.

In some embodiments, the obtained mangosteen shell extract may be further used as a food additive to make a food composition containing the mangosteen shell extract. Herein, the mangosteen shell extract in any embodiment can be added during the preparation of a raw material by a conventional method, or the mangosteen shell extract in any embodiment can be added during the preparation of food by a conventional method, to be formulated with any edible material into an edible product (that is, a food composition) for ingestion by humans and non-human animals.

In some embodiments, a dosage form of the composition may be liquid or solid (for example, powder or tablets).

In some embodiments, a dose of the composition is 2 g/day of liquid mangosteen shell extract.

In some embodiments, a dose of the composition is 0.2 g/day of solid mangosteen shell extract.

Example 1: Preparation of the Mangosteen Shell Extract

A mangosteen shell was coarsely crushed into a mangosteen shell raw material of about 12 mm in size and then mixed with an enzyme solution at a weight ratio of 1:4 for a subsequent two-stage extraction step. The enzyme solution is an aqueous solution containing 0.5 wt % of glucoamylase prepared by dissolving glucoamylase (purchased from TRUMP chemical corp.) in RO water. The enzyme solution was heated to 55±5° C., and then the mangosteen shell raw material was added in the enzyme solution and stirred by using a reflux pump at 3.0±0.5 kg/cm² for extraction for 60 minutes, to obtain a primary extract. Then, after the extraction temperature was increased to 85±5° C., secondary extraction was performed on the primary extract for 60 minutes to obtain a secondary extract, and whether a degree Brix of the obtained secondary extract was greater than 1.3° Bx (detected at 20° C.) was determined. If the degree Brix does not meet the requirement, the extraction may be continued for 30 minutes until it is determined that the degree Brix meets the requirement.

The secondary extract with the required degree Brix was filtered through a 400-mesh filter screen to remove the mangosteen shell raw material, and the filtered secondary extract was concentrated with 1±0.2 kg/cm² vapor at 60±5°

C., until the degree Brix was 6.0±0.5° Bx (detected at 20° C.), to obtain a mangosteen shell extract.

Example 2: Osteoclast Differentiation Experiment

Osteoclasts are multinucleated cells formed through fusion and differentiation of multiple monocytes, and have a main function of breaking down and destroying bone tissue, which are closely related to osteoporosis. Therefore, whether the mangosteen shell extract has an effect of reliev- ing osteoporosis can be estimated by observing a capability of the mangosteen shell extract to inhibit the differentiation of monocytes into osteoclasts.

Cells used herein were peripheral blood mononuclear cells (PBMCs) prepared through centrifugation of peripheral blood obtained from healthy donors. A cell culture medium used herein was the α-MEM medium (Gibco; Cat.12000-022) containing 10% fetal bovine serum (Gibco; Cat. 10437-028) and 1× antibiotics (Gibco; Cat.15240-062). A culture medium used for osteoclast differentiation was the α-MEM medium (Gibco; Cat. 12000-022) containing 10% fetal bovine serum (Gibco; Cat.10437-028), 1× antibiotics (Gibco; Cat.15240-062), 40 ng/ml human RANKL (Peprotech; Cat.310-01), and 25 ng/ml human M-CSF (Peprotech; Cat.300-25).

First, the PBMCs were inoculated into a 24-well culture dish containing 500 μL of the cell culture medium per well in a density of $1\times10^6$ cells/well, and were cultured in a $CO_2$ incubator for 24 h.

The cultured PBMCs were classified into a control group and an experimental group. The culture medium for the PBMCs in each group was replaced with a corresponding experimental culture medium, and then cultured for 14-21 days. The experimental culture medium was replaced every three days, until a required state of osteoclast differentiation in the control group was observed by using a microscope (ZEISS; Cat. Vert.A1). Herein, the experimental culture medium in the control group is the culture medium used for osteoclast differentiation, and the experimental culture medium in the experimental group is the culture medium used for osteoclast differentiation containing 0.03125 mg/mL of the mangosteen shell extract prepared in Example 1.

One drop of ActinRed™ 555 ReadyProbes™ reagent (Thermo; Cat.R37112) and Hoechst 33342 stain (purchased from Thermo; No. Cat.62249; 1:20000 dilution) were added to both the control group and the experimental group to react in the dark for 15 minutes, to stain actin and cells. Then, the morphology and nucleus quantity of osteoclasts were observed and photographed in the dark by using a fluores- cence microscope (inverted microscope with a camera sys- tem; ZEISS; Cat. Vert.A1), to determine a capability of a sample to inhibit osteoclast differentiation. The photo- graphic results were shown in FIG. 2.

Referring to FIG. 2, the left panel shows a fluorescence photograph of the control group, and the right panel showed a fluorescence photograph of the experimental group. The blue circle indicated the nucleus, the orange color indicated the actin, and the red arrow indicated the osteoclast. An undifferentiated PBMC was small in size, and actin was expressed in the whole cell, so punctiform fluorescence could be seen after staining, as shown in the experimental group in the right panel of FIG. 2. However, PBMCs were differentiated due to stimulation of osteoclast differentiation factors and fused together to form a large and multinucleated osteoclast, and actin formed a clear ring-like structure at the edge of the cell, so ring-like fluorescence could be seen at the edge of the cell after staining, as shown in the control group in the left panel of FIG. 2. Therefore, it could be learned from FIG. 2 that the mangosteen shell extract inhibited PBMCs from stimulation of osteoclast differentia- tion factors, thereby inhibiting osteoclast differentiation, reducing bone metabolism, strengthening bones, and pre- venting bone loss.

Example 3: Polyglucosamine Secretion Experiment

Cells used herein were ATDC5 cells (ATCCRCRL-2846™), which were chondrogenic cells. A cell culture medium used herein was the DMEM:Ham's F12 (1:1) medium (purchased from Gibco) containing 2 mM L-glu- tamine (purchased from Gibco), 5% fetal bovine serum (FBS, purchased from Gibco), and 1% penicillin/streptomy- cin antibiotic combination (purchased from Gibco). A cul- ture medium used for chondrocyte differentiation was the DMEM:Ham's F12 (1:1) medium (purchased from Gibco) containing 1% insulin-transferrin-selenium (purchased from Gibco), 2 mM L-glutamine (purchased from Gibco), 5% fetal bovine serum (FBS, purchased from Gibco), and 1% penicillin/streptomycin antibiotic combination (purchased from Gibco).

First, $1\times10^5$ ATDC5 cells were inoculated into a 6-well culture dish containing 2 mL of the cell culture medium per well, and were cultured in a 37° C. incubator for 24 h. The cell culture medium was changed every three days until the dish was completely covered by the cells.

The ATDC5 cells were classified into a control group and an experimental group. The cell culture medium was replaced with an experimental culture medium, and then cultured for differentiation for 35 days. The experimental culture medium was replaced every three days. Herein, the experimental culture medium in the control group is the culture medium used for chondrocyte differentiation, and the experimental culture medium in the experimental group is the culture medium used for chondrocyte differentiation containing 0.03125 mg/ml of the mangosteen shell extract prepared in Example 1.

After differentiation was completed, the experimental culture media in the two groups were removed, and the cells in the two groups were rinsed with 1×PBS for three times. Then, 0.5 mL of 10% formaldehyde (purchased from Echo chemical, Taiwan, Cat. TG1794-4-0000-72NI) was added to react at room temperature for 30 minutes to fix the cells. Then, after the formaldehyde was removed, the cells were rinsed with 1×PBS for three times.

Then, 0.5 mL of 1% Alcian blue solution (pH 2.5; prepared in 0.1 M HCl) was added in each well of the culture dish for staining overnight at room temperature. After stain- ing was completed, the cells were rinsed with 1×PBS for three times, and blue signals presented by polyglucosamine stained with Alcian blue were observed by using a micro- scope (ZEISS). The results were shown in FIG. 3.

Figure 3:
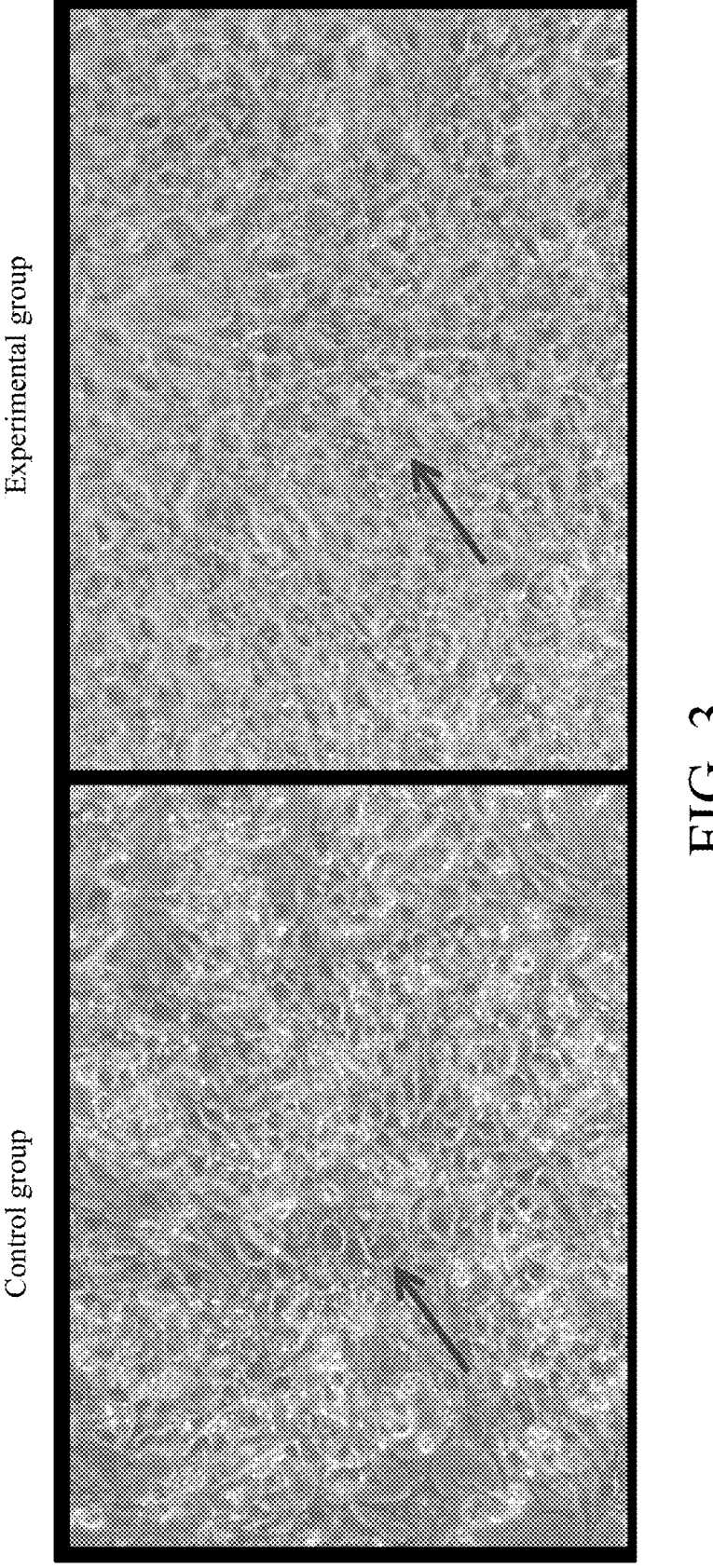
FIG. 3 shows photographs of an experimental group and a control group in a polyglucosamine secretion experiment.

Referring to FIG. 3, the left panel showed a photograph of the control group, and the right panel shows a photograph of the experimental group. The intercellular blue background signal indicated polyglucosamine, and the red arrow indi- cated the chondrocyte obtained through differentiation of ATDC5 cells. When chondrogenic cells differentiate into mature chondrocytes, the chondrocytes had a capability of producing polyglucosamine. Therefore, by comparing the blue background signals of the experimental group and the control group in FIG. 3, it could be learned that the addition of the mangosteen shell extract promote the differentiation of ATDC5 cells into chondrocytes, and produce more polyglucosamine. Polyglucosamine is a major component of cartilage and joint fluid. Aging or overuse of joints may cause cartilage wear and tear and insufficient joint fluid, resulting in narrowing of the spacing between the joints. In addition, accumulated wear and tear may cause joint friction, which may lead to inflammation, swelling, and pain in the joints in severe cases. Therefore, since polyglucosamine is related to joint health, after the mangosteen shell extract is administered to a subject, more polyglucosamine can be produced, so that joint discomfort can be relieved, pain caused by joint wear and tear can be relieved, joint degeneration can be avoided, and occurrence of arthritis can be reduced.

Example 4: Calcium Absorption Experiment

Cells used herein were human intestinal cells (hereinafter referred to as C2BBel cells; ATCC CRL-2102), which are chondrogenic cells. A cell culture medium used herein was the Dulbecco's Modified Eagle medium (purchased from Gibco, Cat. 12100-038) containing 10% fetal bovine serum (FBS, purchased from Gibco, Cat. 10438-026) and 1% penicillin/streptomycin antibiotic combination (purchased from Gibco, Cat. 15140-122).

First, $2 \times 10^5$ C2BBel cells were inoculated into a 6-well culture dish containing 2 mL of the cell culture medium per well, and were cultured in a 37° C. incubator for 24 h.

The cultured C2BBel cells were classified into a control group and an experimental group. The cell culture medium in each group was replaced with an experimental culture medium, and then cultured for 1 h. Herein, the experimental culture medium in the control group is the cell culture medium, and the experimental culture medium in the experimental group is the cell culture medium containing 0.0625 mg/mL of the mangosteen shell extract prepared in Example 1.

2 µM Fluo-4 AM calcium indicator (purchased from Invitrogen) was added to each group and cultured at room temperature for 45 minutes. Then, the cells were washed once with 1×PBS, the cell culture medium was then added, and fluorescence expression of the C2BBel cells in the two groups was observed by using a fluorescence microscope (Zeiss). Stronger fluorescence expression of the C2BBel cells indicates more calcium ions in the C2BBel cells. The results were shown in FIG. 4.

Figure 4:
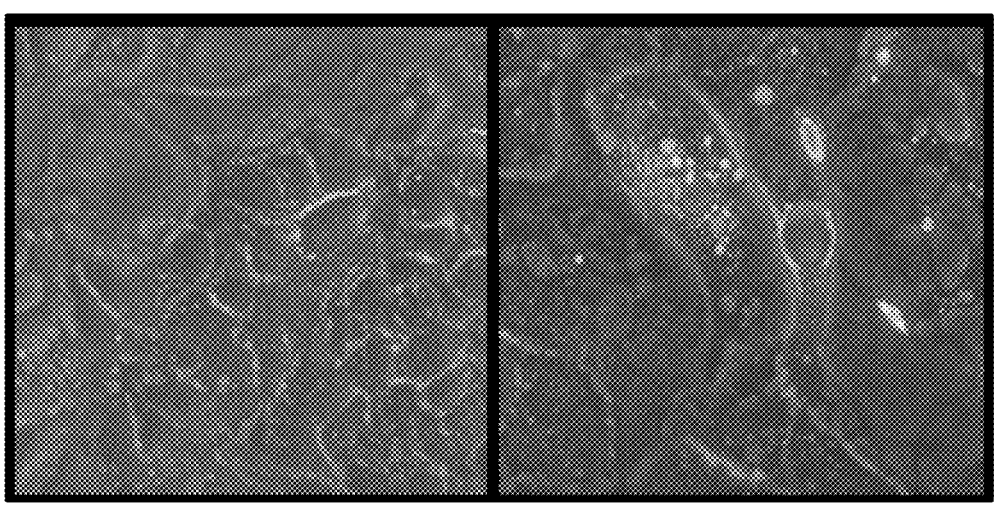
FIG. 4 shows photographs of an experimental group and a control group in a calcium absorption experiment.

Referring to FIG. 4, the left panel showed a fluorescence photograph of the control group, and the right panel showed a fluorescence photograph of the experimental group. The green fluorescence indicates calcium ions. Therefore, it could be learned from FIG. 4 that the mangosteen shell extract increase the amount of calcium indicator in the intestinal cells.

Then, each group was subjected to trypsin digestion to collect the C2BBel cells in each group. The C2BBel cells were centrifuged at 300×g for 5 minutes to collect a C2BBel cell precipitate in each group. Then, the C2BBel cell precipitate was redissolved in 500 µL of 2% FBS, to obtain a to-be-tested sample in each group. Then, after the to-be-tested sample in each group was processed with the Fluo-4 AM calcium indicator (purchased from Invitrogen), an absorbance value at an excitation/scattering (Ex/Em) wavelength of 494/506 nm was measured by using a flow cytometer (manufacturer:BD Accuri C6 Plus), to determine a calcium absorption amount of the intestinal cells. Herein, a value of the control group was considered as 100% of relative calcium absorption amount to determine a relative calcium absorption amount of the experimental group. The results were shown in FIG. 5. In this figure, "*" indicates that the p value is less than 0.05.

Figure 5:
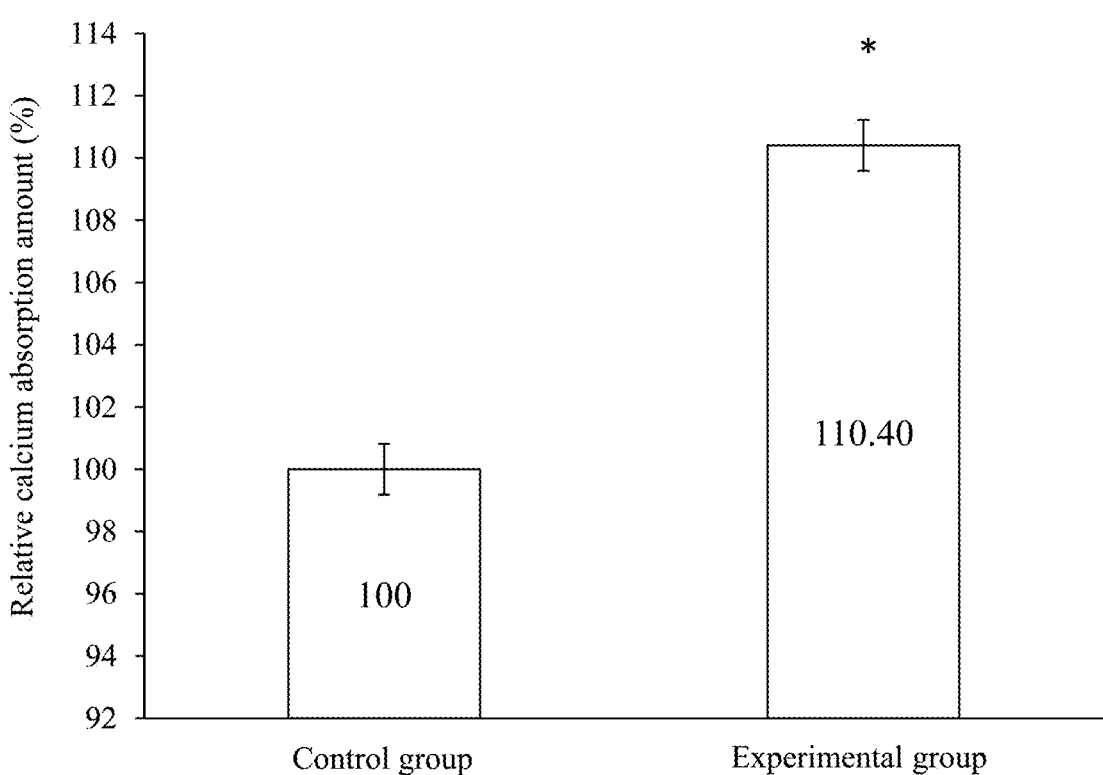
FIG. 5 shows a bar chart of a calcium absorption experiment.

Referring to FIG. 5, the relative calcium absorption amount of the control group was 100%, the relative calcium absorption amount of the experimental group was 110.4%, and the calcium absorption amount of the experimental group was increased by about 10% compared with the control group. It could be learned from above that the mangosteen shell extract increase the relative calcium absorption amount of the C2BBel cells. In other words, when the mangosteen shell extract is administered to a subject, intestinal cells of the subject can absorb more calcium, which helps avoid non-absorption of calcium by bones to maintain a normal blood calcium concentration, and can strengthen bone quality and bones and prevent bone loss.

Example 5: Human Body Test

By self control, changes in bone health effects were compared before and after a composition containing the mangosteen shell extract was administered to eight subjects. The used composition was a 50 ml bottle of mangosteen shell extract drink, and each bottle of mangosteen shell extract drink contained 2 g of mangosteen shell extract and 48 g of water.

Test method: The eight subjects drank one bottle of mangosteen shell extract drink daily for 12 weeks. Bone density detection was performed by using a dual energy X-ray absorptiometer (DXA) in the Cathay Health Management Center before drinking (week 0), after eight weeks of drinking (week 8), and after 12 weeks of drinking (week 12). Fasting blood was collected before drinking (week 0) and after 12 weeks of drinking (week 12) for blood detection in the Lezen Reference Lab. The eight subjects were aged between 25 and 55 years old and regularly drank coffee and/or carbonated beverages.

Blood detection items included a blood osteogenesis indicator (HB0699 by the Lezen Reference Lab) and a blood inflammation indicator (HE0106 by the Lezen Reference Lab). The blood osteogenesis indicator was the concentration of osteocalcin. The blood inflammation indicator is the concentration of high-sensitivity C-reactive protein (hs-CRP).

A bone density detection item was presented by a T score in an instrumental measurement table. The T score was an indicator for determining bone density. A T score normal value of bone density was between −1 and 1. If the T score value is less than −1, it indicated osteopenia, that is, low bone density. If the T score value was less than or equal to −2.5, it indicates osteoporosis.

Example 5-1: Detection of Osteocalcin in Blood

Figure 6:
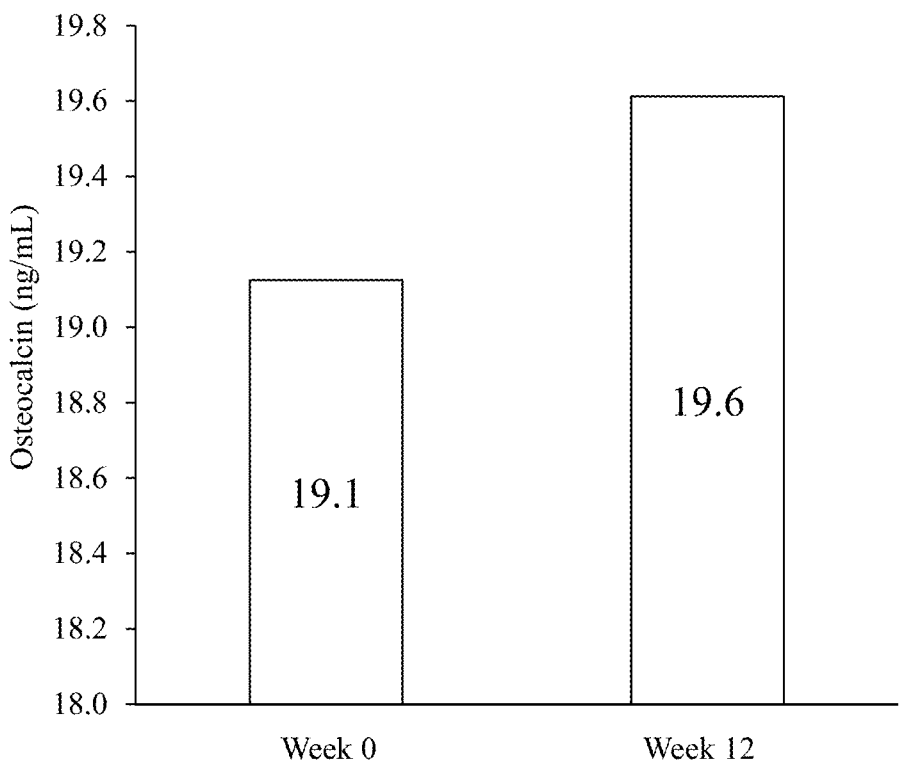
FIG. 6 shows a bar chart of average osteocalcin secretion level of subjects at week 0 and week 12.

Referring to FIG. 6, a mean osteocalcin concentration in the blood of the eight subjects at week 0 was 19.1 ng/ml, and a mean osteocalcin concentration in the blood of the eight subjects after 12 weeks of drinking the mangosteen shell extract drink containing the mangosteen shell extract was increased to 19.6 ng/ml. It indicated that the mean osteocalcin concentration in the blood of the eight subjects after 12 weeks of drinking the mangosteen shell extract was increased by 2.6%, and a percentage of improvement was 62.5% (five subjects).

It could be learned that the administration of the mangosteen shell extract increase the osteocalcin concentration in the blood, further helping bone formation, increasing bone density, strengthening bone quality and bones, and preventing bone loss.

Example 5-2: Detection of Inflammation Indicator in Blood

Figure 7:
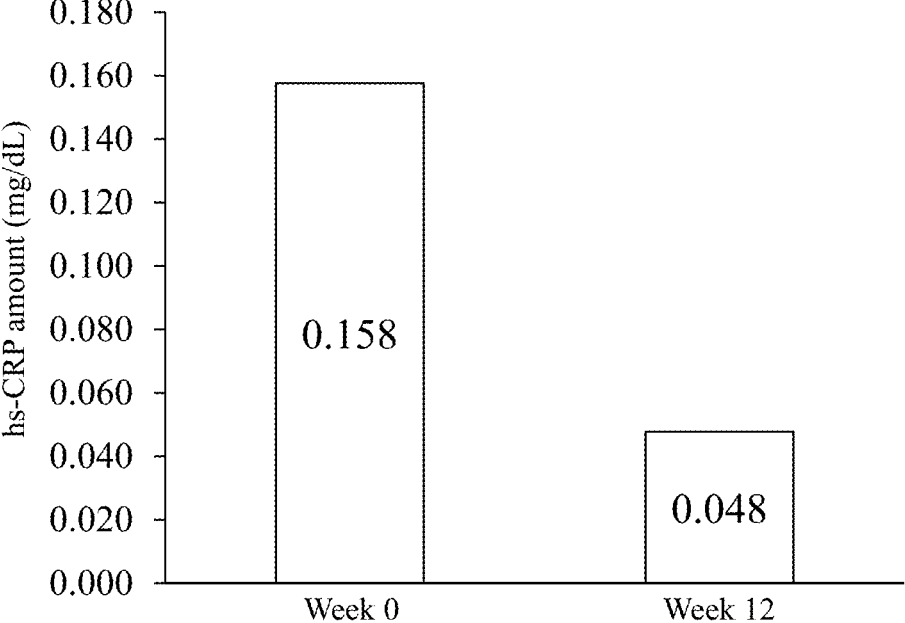
FIG. 7 shows a bar chart of average inflammation indicator level in the body of subjects at week 0 and week 12.

Referring to FIG. 7, a mean hs-CRP amount in the blood of the eight subjects at week 0 was 0.158 mg/dL, and a mean hs-CRP amount in the blood of the eight subjects after 12 weeks of drinking the mangosteen shell extract drink containing the mangosteen shell extract is reduced to 0.048 mg/dL. It indicated that the mean hs-CRP amount in the blood of the eight subjects after 12 weeks of drinking the mangosteen shell extract was reduced by 69.6%, and a percentage of improvement was 75% (six subjects).

It could be learned that the administration of the mangosteen shell extract relieve inflammation, and prevent inflammation caused by joint wear and tear or prevent joint pain caused by inflammation due to articular cartilage wear and tear.

Example 5-3: Detection of Bone Density

Figure 8:
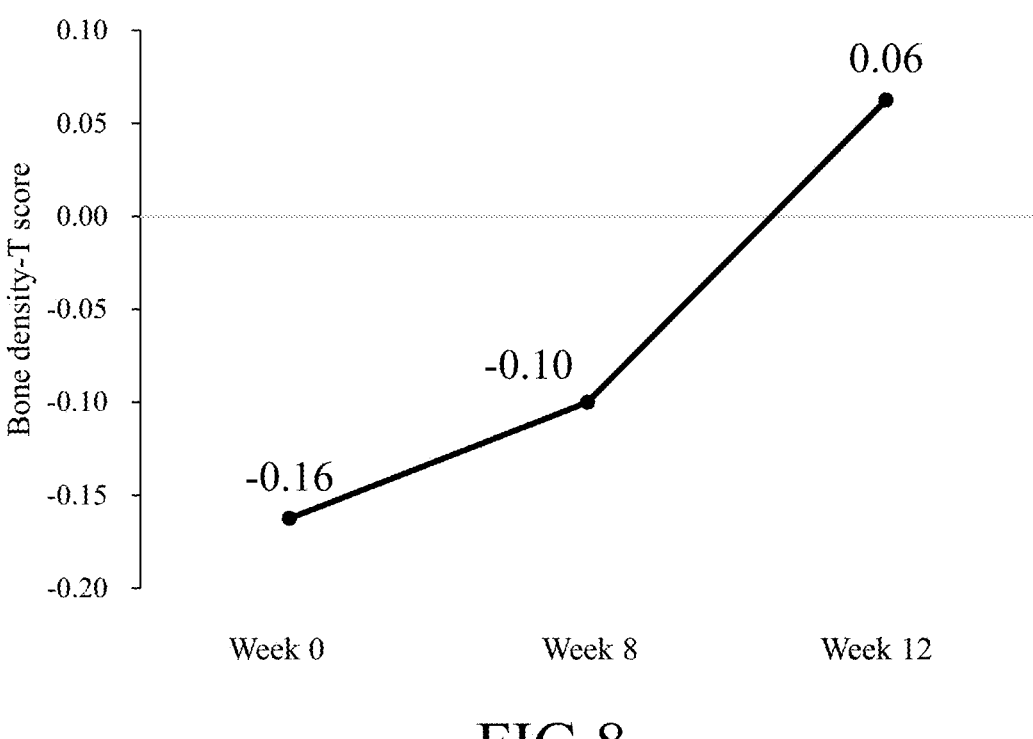
FIG. 8 shows a line chart of average bone density level of subjects at week 0, week 8, and week 12.

Referring to FIG. 8, a mean T score of the eight subjects at week 0 was −0.16, a mean T score at week 8 was −0.10, and a mean T score at week 12 was 0.06. It could be learned that the bone density of the eight subjects at week 0 was between −1 and 1, indicating that the eight subjects have normal bone density. After 12 weeks of drinking the mangosteen shell extract, the T score of the eight subjects was increased by 0.22. It indicated that the average bone quality is increased, that is, the bone density was increased. In other words, the administration of the mangosteen shell extract can increase bone density, prevent bone loss, and strengthen bones.

Figure 9:
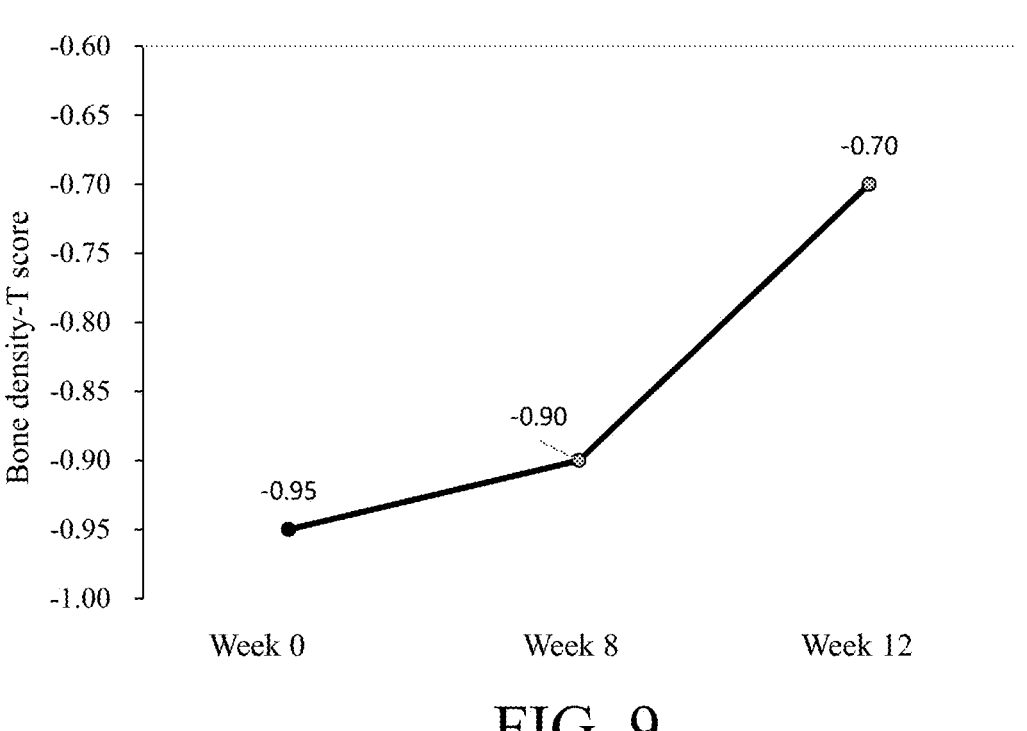
FIG. 9 shows a line chart of average bone density level of subjects with low bone density at week 0, week 8, and week 12.

Four of the eight subjects had the T score less than 0.0 at week 0, indicating that they have low bone density. The detection results of the four subjects were shown in FIG. 9. Referring to FIG. 9, a mean T score of the four subjects at week 0 was −0.95, which was the normal value of bone density between −1 and 1, and was close to low bone density. A mean T score at week 8 was −0.9, and a mean T score at week 12 was −0.7. It could be learned that, after 12 weeks of drinking the mangosteen shell extract, the T score of the four subjects was increased by 0.25. It indicated that the average bone quality was increased, that is, the bone density was increased. In other words, the administration of the mangosteen shell extract can help increase bone density and strengthen bones.

From the above, it could be learned that 12 weeks of drinking the mangosteen shell extract increase the osteocalcin concentration in the blood of the subjects, relieve inflammation in the subjects, and increase the bone density value of the subjects, indicating that the mangosteen shell extract has functions of reducing inflammation and improving bone health.

Based on the above, the method for improving bone health according to any embodiment of the present disclosure is implemented by using the mangosteen shell extract prepared by a two-stage extraction at different extraction temperatures. The two-stage extraction at different extraction temperatures can fully release and retain the active ingredients from the mangosteen shell and further increase the contents of the active ingredients in the mangosteen shell extract. In addition, the mangosteen shell extract has the effects of strengthening bones, preventing joint wear and tear, preventing bone loss, increasing bone density, improving calcium absorption, relieving inflammation in the body, and preventing inflammation caused by joint wear and tear.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for improving bone health, comprising administering to a subject in need thereof a composition comprising a mangosteen shell extract, wherein the mangosteen shell extract is prepared by performing a two-stage extraction on a fruit shell of mangosteen using an enzyme solution at different extraction temperatures sequentially.

2. The method according to claim 1, wherein the mangosteen shell extract has a total flavonoid content of at least 19000±5000 ppm.

3. The method according to claim 1, wherein the enzyme solution is an aqueous solution comprising 0.1-1 wt % of diastase.

4. The method according to claim 3, wherein the diastase is glucoamylase, α-amylase, β-amylase, isoamylase, or any combination thereof.

5. The method according to claim 1, wherein the extraction temperatures for the two-stage extraction are 45° C. to 65° C. and 75° C. to 95° C., respectively.

6. The method according to claim 5, wherein the extraction temperatures for the two-stage extraction are 55±5° C. and 85±5° C., respectively.

7. The method according to claim 1, wherein extraction time at each stage of the two-stage extraction is 60 minutes to 90 minutes.

8. The method according to claim 1, wherein performing the two-stage extraction comprises the following steps:

performing a primary extraction on the fruit shell of mangosteen with the enzyme solution at 45° C. to 65° C. for 60 minutes to obtain a primary extract;

performing a secondary extraction on the primary extract at 75° C. to 95° C. for 60 minutes to 90 minutes to obtain a secondary extract; and filtering and concentrating the secondary extract to obtain the mangosteen shell extract.

9. The method according to claim 1, wherein the bone health is bone strengthening, joint wear and tear prevention, and/or bone loss prevention.

10. The method according to claim 1, wherein the mangosteen shell extract has at least one of the following functions: inhibiting osteoclast differentiation, increasing bone density, promoting intestinal calcium absorption, promoting osteocalcin secretion, and anti-inflammation, so as to strengthen the bones.

11. The method according to claim 1, wherein the mangosteen shell extract is used for at least one of the following functions: promoting polyglucosamine expression and reducing inflammation, so as to prevent joint wear and tear.

12. The method according to claim 1, wherein the mangosteen shell extract is used for at least one of the following functions: inhibiting osteoclast differentiation and promoting osteocalcin secretion, so as to prevent bone loss.

13. The method according to claim 1, wherein the mangosteen shell extract has a function of relieving inflammation in the body of the subject in need thereof.

* * * * *